United States Patent [19]

Schroeder

[11] Patent Number: 4,629,715

[45] Date of Patent: Dec. 16, 1986

[54] PURIFICATION OF TEREPHTHALIC ACID TO RELATIVELY LOW LEVELS OF 4-CARBOXYBENZALDEHYDE AND CATALYST THEREFOR

[75] Inventor: Hobe Schroeder, Warrenville, Ill.

[73] Assignee: Amoco Corporation, Chicago, Ill.

[21] Appl. No.: 785,321

[22] Filed: Oct. 7, 1985

[51] Int. Cl.$^4$ .......................... B01J 23/44; B01J 23/46; C07C 51/42
[52] U.S. Cl. .................................... 502/185; 562/485; 562/486; 562/487
[58] Field of Search ....................... 562/485, 486, 487; 502/185

[56] References Cited

U.S. PATENT DOCUMENTS

| | | | |
|---|---|---|---|
| 3,546,285 | 12/1970 | Witt | 562/487 |
| 3,584,039 | 6/1971 | Meyer | 562/487 X |
| 3,639,465 | 2/1972 | Olsen et al. | 562/487 |
| 3,726,915 | 4/1973 | Pohlmann | 562/487 |
| 4,126,638 | 11/1978 | Alagy et al. | 562/487 |
| 4,405,809 | 9/1983 | Stech et al. | 562/487 |

Primary Examiner—Natalie Trousof
Assistant Examiner—Vera C. Clarke
Attorney, Agent, or Firm—James R. Henes; William T. McClain; William H. Magidson

[57] ABSTRACT

Aqueous solutions of crude terephthalic acid are purified to relatively low 4-carboxybenzaldehyde levels under hydrogenation conditions by using a layered catalyst bed. The aqueous terephthalic acid solution to be purified is first passed through a particulate primary catalyst layer constituted by palladium on active carbon and thereafter through a particulate secondary catalyst bed constituted by rhodium on active carbon.

17 Claims, 2 Drawing Figures

PURIFICATION OF TEREPHTHALIC ACID TO RELATIVELY LOW LEVELS OF 4-CARBOXYBENZALDEHYDE AND CATALYST THEREFOR

TECHNICAL FIELD

This invention relates to a method for purification of terephthalic acid to a relatively low 4-carboxybenzaldehyde level, and to means for effecting such purification.

BACKGROUND OF THE INVENTION

Polymer grade terephthalic acid (TA) is the starting material for polyethylene terephthalate (PET), which is the principal polymer for polyester fibers, polyester films, and resins for bottles and the like containers. Polyester fibers are used in textiles as well as in industrial applications such as tire cord. Polyester films coated with adhesives and emulsions are useful as wrapping tapes, photographic films, recording tapes, and the like.

Polymer grade terephthalic acid is derived from relatively less pure, technical grade terephthalic acid by purification of the latter utilizing hydrogen and a noble metal catalyst as described in U.S. Pat. No. 3,584,039 to Meyer. In the purification process, the impure terephthalic acid is dissolved in water at an elevated temperature, and the resulting solution hydrogenated, preferably in the presence of a hydrogenation catalyst, e.g., palladium on a carbon support, as described in U.S. Pat. No. 3,726,915 to Pohlmann. This hydrogenation step converts the various color bodies present in the relatively impure terephthalic acid to colorless products. The principal feedstock impurity, 4-carboxybenzaldehyde (4-CBA), is converted to p-toluic acid (TOL). Color-forming precursors and color bodies present as impurities are believed to be of the benzil, fluorenone and/or anthraquinone type.

The resulting purified product, polymer grade terephthalic acid, is recovered by crystallization, centrifugation, and drying. Another related purification-by-hydrogenation process for aromatic polycarboxylic acids produced by liquid phase catalytic oxidation of polyalkyl aromatic hydrocarbons is described in U.S. Pat. No. 4,405,809 to Stech et al.

At 4-CBA concentrations of about 100 parts per million, by weight, of TA, however, the rate of reduction of 4-CBA to TOL slows down considerably. The reduction rate may stop altogether at certain reaction conditions. Inasmuch as unreduced or partially reduced 4-CBA subsequently co-crystallizes with TA, a TA product that contains undesirable impurities is obtained.

Moreover, Pd/C catalyst beds become less active as they are used. Eventually such beds must be taken out of service as product specifications for purified TA are exceeded.

Accordingly, it would be desirable to reduce the overall 4-CBA level in purified TA and to extend the useful life of a Pd/C catalyst bed for producing purified TA having a specified low level of 4-CBA derived impurities. The present invention satisfies both of the foregoing desiderata.

SUMMARY OF THE INVENTION

The present invention contemplates the purification of relatively impure aqueous solutions of terephthalic acid by hydrogenation in a layered particulate catalyst bed to a relatively low 4-carboxybenzaldehyde level. The layered particulate catalyst bed includes a primary layer constituted by palladium supported on an active carbon carrier and a secondary layer, downstream from the primary layer, constituted by rhodium supported on an active carbon carrier.

According to the present invention, a relatively impure aqueous terephthalic acid solution containing up to about 10,000 parts by million, by weight, of 4-carboxybenzaldehyde is hydrogenated in a liquid-filled, layered catalyst bed arranged so that the hydrogenated aqueous terephthalic acid solution leaving a Pd/C catalyst layer next enters a Rh/C catalyst layer.

In the Pd/C catalyst layer the hydrogenation is carried out at a temperature of about 100° C. to about 350° C. and at a pressure sufficient to maintain the solution in liquid phase, usually of about 200 psig to about 1,500 psig. The hydrogenated and further purified aqueous solution, i.e., the liquid effluent from the catalyst bed, is thereafter cooled to effect separation of relatively high purity terephthalic acid from the solution by crystallization.

DESCRIPTION OF PREFERRED EMBODIMENTS

Figure 1:
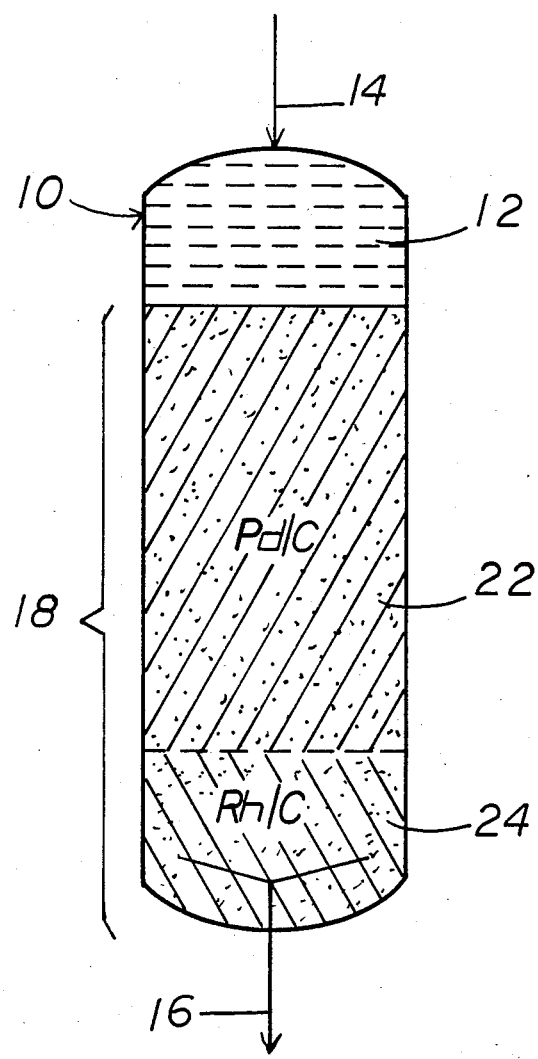
FIG. 1 is a diagrammatic depiction of a down-flow reactor having a layered particulate catalyst bed embodying the present invention.

Relatively impure, i.e., crude, terephtalic acid (TA) is obtained by a liquid phase oxidation of a para-dialkylbenzene such as p-xylene. The obtained product is an aqueous TA solution that includes relatively large amounts of impurities such as 4-carboxybenzaldehyde (4-CBA) which can be present in amounts up to about 10,000 parts per million (ppm) parts of terephthalic acid, by weight. These impurities adversely affect terephthalic acid polymerization reactions to produce polyethylene terephthalate (PET) as well as cause undesirable coloring of the resulting PET polymers. Heretofore a practical limit for 4-CBA content of aqueous TA solutions purified by hydrogenation in production quantities has been about 100 ppm, based on TA.

The process embodying the present invention is conducted at an elevated temperature and pressure in a fixed catalyst bed that is layered. Both down-flow and up-flow reactors can be used. The terephthalic acid to be purified is dissolved in water or a like polar solvent. Water is the preferred solvent; however, other suitable polar solvents are the relatively lower molecular weight alkyl carboxylic acids, alone or admixed with water.

Reactor, and thus TA solution, temperatures during purification can be in the range of about 100° C. (about 212° F.) to about 350° C. (about 660° F.). Preferably the temperatures are in the range of about 275° C. (about 530° F.) to about 300° C. (about 572° F.).

Reactor pressure conditions primarily depend upon the temperature at which the purification process is carried out. Inasmuch as the temperatures at which practical amounts of the impure terephthalic acid may be dissolved are substantially above the normal boiling point of the polar solvent, the process pressures are necessarily considerably above atmospheric pressure to maintain the solution in liquid phase. If the reactor is hydraulically full, the reactor pressure can be controlled by the feed pumping rate. If the reactor has a head space, the reactor pressure can be maintained by gaseous hydrogen alone or in admixture with an inert gas such as water vapor and/or nitrogen in the head space. The use of an inert gas in admixture with hydrogen also can provide an advantageous means for modulating the reactor hydrogen partial pressure, especially at relatively low hydrogen partial pressures. To this end, the inert gas preferably is admixed with hydrogen prior to introduction into the reactor. In general, the reactor pressure during hydrogenation can be in the range of about 200 to about 1500 pounds per square inch gauge (psig), and usually is in the range of about 900 psig to about 1,200 psig.

The hydrogenation reactor can be operated in several modes. For example, a predetermined liquid level can be maintained in the reactor and hydrogen can be fed in, for any given reactor pressure, at a rate sufficient to maintain the predetermined liquid level. The difference between the actual reactor pressure and the vapor pressure of the terephthalic acid solution present is the hydrogen partial pressure in the reactor vapor space. Alternatively, if hydrogen is fed in admixture with an inert gas such as nitrogen, the difference between the actual reactor pressure and the vapor pressure of the terephthalic acid solution present is the combined partial pressure of hydrogen and the inert gas admixed therewith. In this case the hydrogen partial pressure can be calculated from the known relative amounts of hydrogen and inert gas present in the admixture.

In yet another operating mode the reactor can be filled with the terephthalic acid solution so as to provide no reactor vapor space. That is, the reactor can be operated as a hydraulically full system with dissolved hydrogen being fed to the reactor by flow control. In such an instance, the solution hydrogen concentration can be modulated by adjusting the hydrogen flow rate to the reactor. If desired, a pseudo-hydrogen partial pressure value can be calculated from the solution hydrogen concentration which, in turn, can be correlated with the hydrogen flow rate to the reactor.

In the operating mode where process control is effected by adjusting the hydrogen partial pressure, the hydrogen partial pressure in the reactor preferably is in the range of about 10 psi to about 200 psi, or higher, depending upon the service pressure rating of the reactor, the degree of contamination of the impure terephthalic acid, the activity and age of the particular catalyst employed, and like processing considerations.

In the operating mode where process control is effected by adjusting directly the hydrogen concentration in the feed solution, the latter usually is less than saturated with respect to hydrogen and the reactor itself is hydraulically full. Thus an adjustment of the hydrogen flow rate to the reactor will result in the desired control of hydrogen concentration in the solution.

In purifying aqueous TA solutions that contain 4-CBA according to the present invention, the solution is first passed through the Pd/C catalyst layer and then through the Rh/C catalyst layer. The following principal reactions are believed to occur. In the Pd/C catalyst layer, 4-CBA is believed to be converted to TOL as follows:

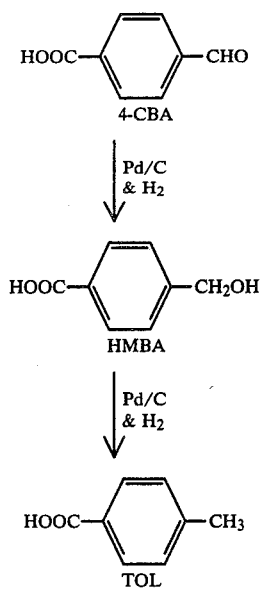

Subsequently, in the secondary, Rh/C catalyst layer downstream from the primary, Pd/C catalyst layer, most if not all of the residual 4-CBA is believed to be decarbonylated to benzoic acid (BA) in the following manner:

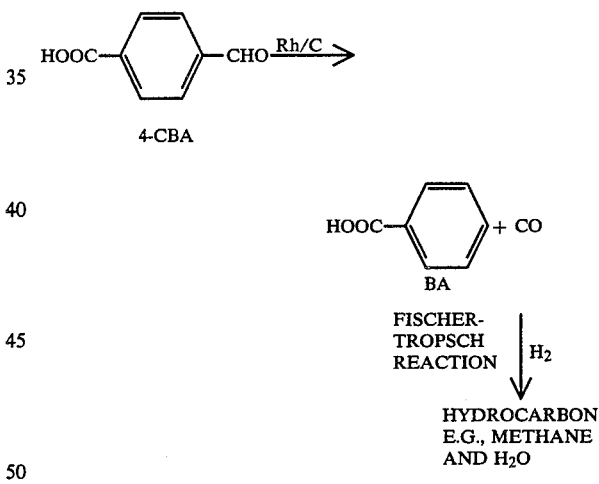

Some decomposition of the TA to BA and some hydrogenation of TA to 4-CBA may also occur; however, both of these are believed to be minor reactions. Thus, a substantial amount of 4-CBA present in the crude TA is hydrogenated to TOL in the primary Pd/C catalyst layer while most of the remainder is decarbonylated to BA in the secondary Rh/C catalyst layer downstream from the primary Pd/C catalyst layer. BA is a by-product that is quite soluble in water and can be readily separated from TA during crystallization and the harvesting of the produced TA crystals.

The presence of carbon monoxide in a 4-CBA hydrogenation reactor is recognized by the prior art to be a problem (see, for example, U.S. Pat. No. 4,201,872 to Kimura) because carbon monoxide is known to inhibit the activity of hydrogenation catalysts. The present process avoids this problem, however, by maintaining conditions favorable to carbon monoxide generation away from the Pd/C catalyst layer, that is, in the Rh/C catalyst layer downstream therefrom, and by effecting in the Rh/C catalyst layer a conversion of at least a portion of the generated carbon monoxide to a hydrocarbon moiety, e.g., methane, by what is believed to be a Fischer-Tropsch type of reaction. The produced hydrocarbon by-products are inert with respect to the purified TA, are swept from the catalyst bed with the treated effluent stream, and can be readily separated from the resulting reaction product admixture by purging or in any other convenient manner.

Decarbonylation and carbon monoxide conversion to a hydrocarbon moiety are believed to occur substantially simultaneously in the Rh/C catalyst layer of the layered fixed catalyst bed of this invention.

The catalyst carrier is active carbon, usually that derived from coconut charcoal in the form of granules having a surface area of at least about 600 $m^2/g$ ($N_2$; BET Method), preferably about 800 $m^2/g$ to about 1500 $m^2/g$. However, other porous carbonaceous supports or substrates can be used as long as the surface area requirements can be met. In addition to coconut charcoal, activated carbon derived from other plant or from animal sources can be utilized. The same type of active carbon carrier preferably is used for both the Pd/C catalyst layer and the Rh/C catalyst layer in the reactor.

Catalyst metal loading on the carrier for palladium can be in the range of about 0.1 weight percent to about 2 weight percent, based on the total weight of the catalyst, i.e., metal plus active carbon carrier, and calculated as elemental metal. Loading on the carrier for rhodium, on the other hand, can have a broader range, specifically about 0.01 to about 2 weight percent, based on the total weight of the catalyst and calculated as elemental metal. Preferably the rhodium metal loading is about 0.5 weight percent. Such catalysts are commercially available.

A suitable Pd/C catalyst can be obtained, for example, from Engelhard Corporation, Newark, New Jersey, under the designation "Palladium on Activated Carbon Granules (Carbon Code CG-5)." Similarly, suitable Rh/C catalysts can be obtained from Engelhard Corporation, under the designations "Rhodium on Activated Carbon Granules (Carbon Code CG-5)" and "Rhodium on Activated Carbon Granules (Carbon Code CG-21)." Both of these Rh/C catalysts have a BET; $N_2$ surface area of about 1,000 $m^2/gram$ and have a particle size of 4×8 mesh, U.S. Sieve Series. Other suitable Rh/C catalysts of similar size and surface area are available from Johnson Matthey Inc., Seabrook, N.H., under the designation "11766 Rhodium, 1% on Steam Activated Carbon Granules, Anhydrous."

The relative thickness of the particulate catalyst layers in the hydrogenation bed can vary; however, the Pd/C catalyst layer preferably constitutes a major portion of the catalyst bed and the Rh/C catalyst layer constitutes a minor portion of the catalyst bed. The catalyst layers at all times are thick enough to avoid substantial channeling within the layer as the aqueous crude terephthalic acid feed solution is passed therethrough. To that end, and as a practical matter, whatever the catalyst bed diameter, the Rh/C catalyst layer is at least about 50 millimeters (about 2 inches) thick.

Volumetrically, the primary, Pd/C catalyst, layer preferably is about two to about twenty times the volume of the secondary, Rh/C catalyst, layer. That is, the volumetric ratio of the primary catalyst layer to the secondary catalyst layer is about 2:1 to about 20:1. Preferably, this volumetric ratio is about 10:1.

The relative amounts of catalyst metal in the Pd/C layer and the Rh/C layer can vary. Generally, palladium and rhodium in the respective bed layers are present in a mol ratio of about 2:1 to about 100:1, preferably in a mol ratio of about 10:1.

The amount of hydrogen supplied under reaction conditions must be sufficient to achieve the desired degree of hydrogenation of 4-CBA to TOL, and to effect the desired conversion of the generated carbon monoxide to a hydrocarbon moiety.

For conversion of 4-CBA to TOL, the stoichiometric hydrogen requirement is two mols of hydrogen for each mol of 4-CBA so converted. For conversion of 4-CBA to BA, the stoichiometric hydrogen requirement is due to the generated carbon monoxide. For the conversion of all generated carbon monoxide to methane this requirement is three mols of hydrogen for each mol of 4-CBA converted to BA. Preferably the amount of hydrogen supplied to the catalyst bed is about two times that stoichiometrically required for the foregoing principal reactions that are taking place in the catalyst bed.

Space velocity (lbs TA solution/lb catalyst/hr) of the aqueous crude TA solution through the catalyst bed is about 5 $hours^{-1}$ to about 25 $hours^{-1}$, preferably about 10 $hours^{-1}$ to about 15 $hours^{-1}$. The residence time of the TA solution in the catalyst bed varies, depending upon the activity of the catalysts present. In general, however, the residence time of the aqueous TA solution in the Pd/C catalyst layer is about 65 percent to about 95 percent of the total residence time of the aqueous TA solution in the catalyst bed.

A layered catalyst bed suitable for practicing the present invention by the hydrogenation of a relatively impure aqueous solution of TA containing 4-CBA is shown in FIG. 1. Reactor 10 is shown hydraulically full with crude aqueous TA solution 12 that is to be purified. This feed solution enters reactor 10 via conduit 14, and purified aqueous TA solution having a relatively lower 4-CBA content exits reactor 10 at the bottom as an effluent via conduit 16. Fixed particulate catalyst bed 18 is constituted by upper, Pd/C catalyst layer 22 and relatively lower, Rh/C catalyst layer 24.

The present invention is illustrated further by the following examples.

EXAMPLE 1: Comparison of Activities of Pd/C and Rh/C Particulate Catalysts in 4-CBA Conversion The ability of Pd/C and Rh/C catalysts to convert 4-CBA was tested in a titanium autoclave having a volume of about one gallon. Both catalysts had a catalyst metal loading of 0.5 percent by weight and were hot washed and aged in the autoclave for 72 hours in the presence of hydrogen and terephthalic acid.

The Pd/C catalyst was a commercially available catalyst obtained from Engelhard Corporation. The Rh/C catalyst was prepared from rhodium nitrate as a precursor at a pH value of 2 in water and using North American active carbon G-201 as support.

Figure 2:
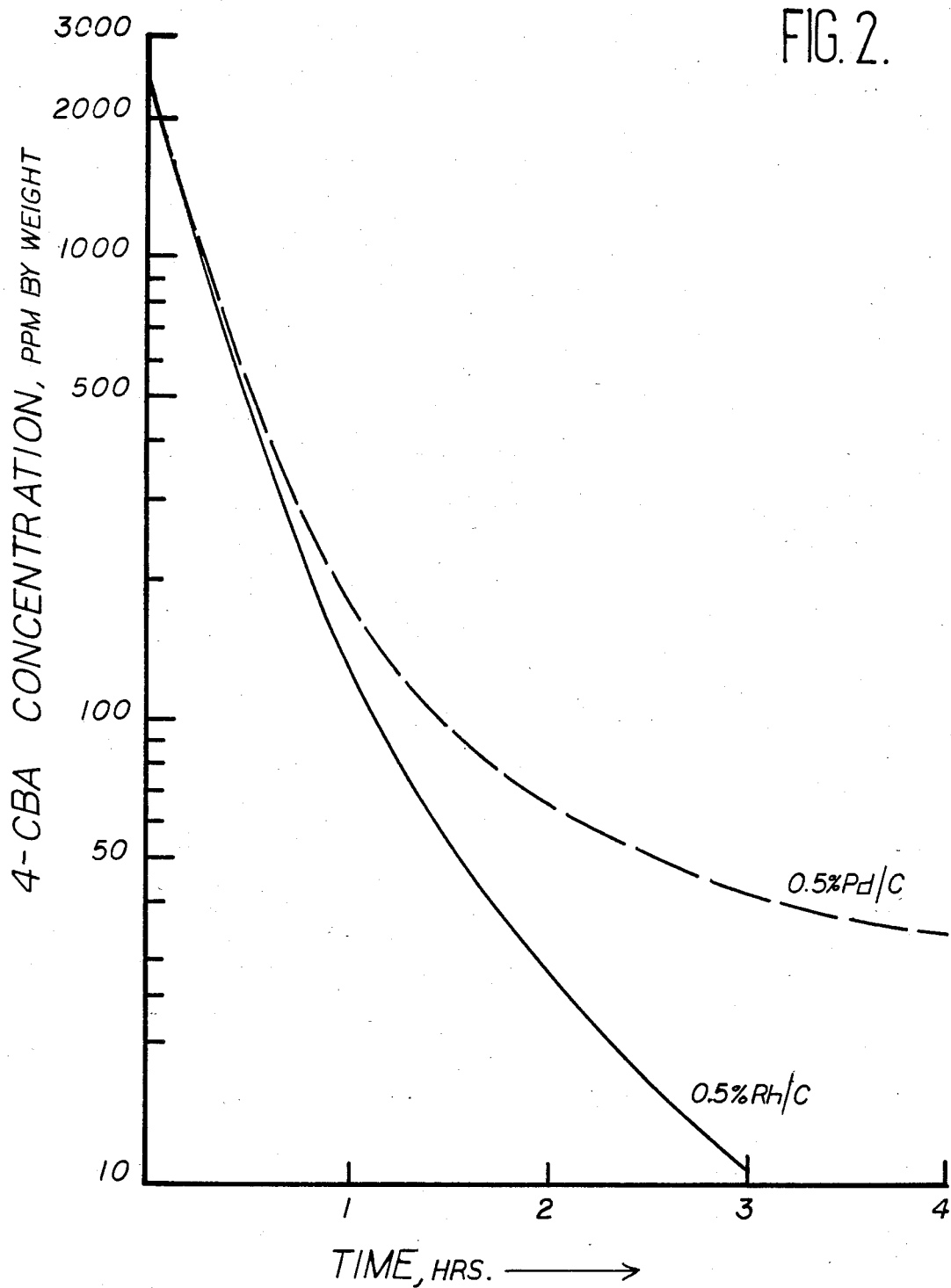
FIG. 2 is a graph showing the conversion of 4-CBA by Pd/C and Rh/C catalysts.

Catalyst activity was ascertained by monitoring the rate of disappearance of 4-CBA in a crude, aqueous TA solution prepared by dissolving crude TA (about 290 grams) in water (about 1190 grams). The prepared solution was charged to the autoclave and maintained at a temperature of about 530° F. Thereafter hydrogen (50 psi at reactor temperature) and catalyst (about 4 grams)

were added to the autoclave. A sample of the crude TA solution was taken prior to catalyst addition and thereafter at periodic intervals, and analyzed for 4-CBA content. The obtained analytical results were then plotted and resulted in the activity profiles shown in FIG. 2 where the activity profile for Pd/C catalyst is shown as an interrupted line and the activity profile for Rh/C catalyst is shown as a continuous line.

EXAMPLE 2: Purification of Crude TA in a Layered, Fixed Catalyst Bed

A pilot plant reactor of the down-flow type, one inch in diameter and equipped with a fixed catalyst bed, was used to purify an aqueous crude terephthalic acid solution (about 12 percent by weight TA) at a temperature of about 280° C. (about 535° F.) and at varying reactor pressures and hydrogen partial pressures. Solution feed rate to the reactor was about 1.6 kilograms of solution per hour.

During one series of runs, the fixed catalyst bed was constituted by 40 grams of a commercial Pd/C catalyst (0.5 wt-% Pd on active carbon support; Engelhard).

During another series of runs, the fixed catalyst bed was layered and was constituted by the aforementioned 40 grams of Pd/C catalyst as an upper catalyst layer and four grams of a particulate Rh/C catalyst (0.1 wt-% Rh; prepared as in Example 1, above) as the bottom catalyst layer.

During yet another series of runs using a layered catalyst bed, the bottom catalyst layer was constituted by a Rh/C catalyst containing 0.5 wt-% Rh and prepared in a manner similar to that used to prepare the 0.1 wt-% Rh/C catalyst.

Catalysts used in these runs were aged for 72 hours in a titanium autoclave in the presence of aqueous TA solution and hydrogen in a manner similar to that of Example 1.

The observed results are compiled in Table I, below.

TABLE I

| | Pilot Plant Evaluation of Rh/C as Bottom Layer in a Pd/C Catalyst Bed | | | | | |
|---|---|---|---|---|---|---|
| | 40 g Pd/C No Rh/C | | 40 g Pd/C 4 g 0.5% Rh/C | | 40 g Pd/C 4 g 0.1% Rh/C | |
| Impurities, | Reactor Press. ($H_2$ pp), psig | | Reactor Press. ($H_2$ pp), psig | | Reactor Press. ($H_2$ pp), psig | |
| ppm by wt. | 1000 (75) | 1050 (125) | 1000 (75) | 1050 (125) | 1000 (75) | 1050 (125) |
| 4-CBA | 20 ± 2 | 11 ± 1 | 8 ± 3 | 5 ± 3 | 6 ± 3 | 3 ± 2 |
| HMBA | 536 | 486 | 247 | 227 | 440 | 329 |
| TOL | 2749 | 3014 | 2876 | 3533 | 2777 | 3258 |
| BA | 648 | 542 | 1202 | 1100 | 1012 | 868 |

The above results demonstrate that a substantial decrease in the 4-CBA concentration in the hydrogenated effluent stream from the reactor is attainable by use of a Rh/C catalyst layer as the last layer with which the stream undergoing treatment is contacted.

The foregoing discussion and the examples are intended as illustrative of the present invention and are not to be taken as limiting. Still other variations within the spirit and scope of this invention are possible and will present themselves to one skilled in the art.

What is claimed is:

1. A method for purification of relatively impure terephthalic acid containing up to about 10,000 parts per million, by weight, of 4-carboxybenzaldehyde which comprises the steps of:

passing an aqueous solution of said impure terephthalic acid, at a temperature of about 100° C. to about 350° C. and at a pressure sufficient to maintain the solution in liquid phase, through a particulate catalyst bed and in the presence of hydrogen; said particulate catalyst bed being a layered bed that includes a primary catalyst layer constituted by palladium supported on an active carbon carrier and a secondary catalyst layer constituted by rhodium supported on an active carbon carrier, and said aqueous solution being first passed through the primary layer of the catalyst bed and then through the secondary layer of the catalyst bed; and thereafter cooling the hydrogenated aqueous solution to effect separation of relatively pure terephthalic acid from said solution by crystallization.

2. The method in accordance with claim 1 wherein the hydrogenation is carried out at a temperature of about 275° C. to about 300° C. and a pressure of about 900 psig to about 1,200 psig, and wherein hydrogen is present in an amount about two times the amount stoichiometrically required.

3. The method in accordance with claim 1 wherein space velocity of the aqueous terephthalic acid solution through the catalyst bed is about 5 hours$^{-1}$ to about 25 hours$^{-1}$.

4. The method in accordance with claim 1 wherein space velocity of the aqueous terephthalic acid solution through the catalyst bed is about 10 hours$^{-1}$ to about 15 hours$^{-1}$.

5. The method in accordance with claim 1 wherein the residence time of the aqueous terephthalic acid solution in said primary catalyst layer is about 65 percent to about 95 percent of the total residence time of the aqueous terephthalic acid solution in the particulate catalyst bed.

6. The method in accordance with claim 1 wherein rhodium is present in the secondary catalyst layer in a concentration of about 0.01 to about 2 percent by weight, based on the total weight of catalyst and calculated as elemental metal.

7. A layered catalyst bed suitable for hydrogenation of a relatively impure aqueous solution of terephthalic acid containing 4-carboxybenzaldehyde which comprises:

a primary catalyst layer constituted by palladium on particulate active carbon carrier; and a secondary catalyst layer downstream from said primary catalyst layer and constituted by rhodium on a particulate active carbon carrier.

8. The layered catalyst bed in accordance with claim 7 wherein said primary catalyst layer constitutes a major portion of the catalyst bed and said secondary catalyst layer constitutes a minor portion of the catalyst bed.

9. The layered catalyst bed in accordance with claim 7 wherein said rhodium is present on its particulate carrier in an amount of about 0.01 to about 2 percent by weight, based on the combined weight of catalyst and calculated as elemental metal.

10. The layered catalyst bed in accordance with claim 7 wherein said rhodium is present on its particulate carrier in an amount of about 0.5 percent by weight, based on the combined weight of carrier and rhodium and calculated as elemental metal.

11. The layered catalyst bed in accordance with claim 7 wherein the secondary catalyst layer is at least about 50 millimeters thick.

12. The layered catalyst bed in accordance with claim 7 wherein the volumetric ratio of the primary catalyst layer to the secondary catalyst layer is about 2:1 to about 20:1.

13. The layered catalyst bed in accordance with claim 7 wherein the volumetric ratio of the primary catalyst layer to the secondary catalyst layer is about 10:1.

14. The layered catalyst bed in accordance with claim 7 wherein the mol ratio of said palladium in the primary catalyst layer to rhodium in the secondary catalyst layer is about 2:1 to about 100:1.

15. The layered catalyst bed in accordance with claim 7 wherein the mol ratio of said palladium in the primary catalyst layer to rhodium in the secondary catalyst layer is about 10:1.

16. The layered catalyst bed in accordance with claim 7 wherein palladium concentration in the primary catalyst layer is about 0.1 to about 2 percent by weight of the respective catalyst, calculated as elemental metal, and wherein rhodium concentration in the secondary catalyst layer is about 0.01 to about 2 percent by weight of the respective catalyst, calculated as elemental metal.

17. The layered catalyst bed in accordance with claim 7 wherein palladium concentration in the primary catalyst layer is about 0.5 percent by weight, calculated as elemental metal, and wherein rhodium concentration in the secondary catalyst layer is about 0.5 percent by weight, calculated as elemental metal.

* * * * *